United States Patent
Kim et al.

(10) Patent No.: US 9,713,645 B2
(45) Date of Patent: Jul. 25, 2017

(54) SHORT INTERFERENCE RNA GENE DELIVERY SYSTEM FOR SYSTEMIC CIRCULATION

(71) Applicant: INDUSTRY-UNIVERSITY COOPERATION FOUNDATION HANYANG UNIVERSITY, Seoul (KR)

(72) Inventors: Yong-Hee Kim, Seoul (KR); Kwang-Suk Lim, Seoul (KR); Hyun-Lin Lee, Seoul (KR)

(73) Assignee: INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 185 days.

(21) Appl. No.: 14/431,586

(22) PCT Filed: Sep. 25, 2013

(86) PCT No.: PCT/KR2013/008560
§ 371 (c)(1),
(2) Date: Jun. 12, 2015

(87) PCT Pub. No.: WO2014/051318
PCT Pub. Date: Apr. 3, 2014

(65) Prior Publication Data
US 2015/0290340 A1    Oct. 15, 2015

(30) Foreign Application Priority Data

Sep. 28, 2012 (KR) .................. 10-2012-0109003
May 28, 2013 (KR) .................. 10-2013-0060230

(51) Int. Cl.
| A61K 47/48 | (2006.01) |
| C07K 7/06 | (2006.01) |
| A61K 31/713 | (2006.01) |
| C12N 15/113 | (2010.01) |
| A61K 31/00 | (2006.01) |
| C12N 15/87 | (2006.01) |

(52) U.S. Cl.
CPC ........ *A61K 47/48215* (2013.01); *A61K 31/00* (2013.01); *A61K 31/713* (2013.01); *A61K 47/48323* (2013.01); *C07K 7/06* (2013.01); *C12N 15/113* (2013.01); *C12N 15/87* (2013.01); *C12N 2310/14* (2013.01); *C12N 2310/3513* (2013.01); *C12N 2310/3515* (2013.01); *C12N 2320/32* (2013.01)

(58) Field of Classification Search
CPC .................. C12N 15/113; C12N 15/87; C12N 2310/3515; C12N 2310/14; C12N 2310/3513; C12N 2310/32; A61K 47/48323; A61K 47/48215; A61K 31/00; A61K 31/713; C07K 7/06; Y10T 428/2982
USPC .................. 428/402; 530/327, 399; 536/24.5
See application file for complete search history.

(56) References Cited

U.S. PATENT DOCUMENTS

| 7,740,880 | B2 | 6/2010 | Kim et al. | |
| 8,058,256 | B2 | 11/2011 | Kim et al. | |
| 8,431,543 | B2* | 4/2013 | Park ....................... | C12N 15/87 514/44 A |
| 2007/0207966 | A1* | 9/2007 | Kim ....................... | C12N 15/87 424/450 |
| 2010/0113559 | A1 | 5/2010 | Park et al. | |
| 2010/0130722 | A1 | 5/2010 | Kim et al. | |
| 2010/0297756 | A1* | 11/2010 | Adib .................. | A61K 48/0041 435/366 |
| 2011/0053829 | A1* | 3/2011 | Baumhof ......... | A61K 47/48215 514/1.2 |
| 2012/0219573 | A1 | 8/2012 | Baumhof et al. | |

FOREIGN PATENT DOCUMENTS

| KR | 10-0825519 B1 | 4/2008 |
| KR | 10-2010-0105674 A | 9/2010 |
| KR | 10-2012-0102586 A | 9/2012 |

OTHER PUBLICATIONS

International Search Report issued Dec. 30, 2013 in PCT/KR2013/008560.
Ayman El-Sayed, et al., "Delivery of Macromolecules using Arginine-Rich Cell-Penetrating Peptides: Ways to Overcome Endosomal Entrapment" The AAPS Journal, vol. 11, No. 1, Mar. 2009, pp. 13-22.

* cited by examiner

*Primary Examiner* — Leszek Kiliman
(74) *Attorney, Agent, or Firm* — Oblon, McClelland, Maier & Neustadt, L.L.P.

(57) ABSTRACT

The present invention relates to a gene delivery system which improves siRNA delivery and the in vivo systemic circulation efficiency thereof More particularly, the present invention is a siRNA gene delivery system for systemic circulation based on polyethylene glycol (PEG) and an arginine 9 (R9) peptide.

10 Claims, 10 Drawing Sheets

(a) Optimization of peg-9R/siVEGF polyplexes formation (b) Stability of peg-9R/siVEGF (charge ratio 9) polyplexes in 90% mouse serum (a) Size of peg-9R/siVEGF polyplexes (b) Zeta potential of peg-9R/siVEGF polyplexes (a) Transfection efficiency of peg-9R/pLuc (c/r 12) - Luciferase assay (b) Cytotoxicity of peg-9R/pLuc (c/r 12) - MTT assay

SHORT INTERFERENCE RNA GENE DELIVERY SYSTEM FOR SYSTEMIC CIRCULATION

TECHNICAL FIELD

The present invention relates to a gene delivery system with improved siRNA delivery and in vivo systemic circulation efficiency. More specifically, the present invention relates to a siRNA delivery system for systemic circulation based on polyethylene glycol (PEG) and a nona-arginine (R9) peptide.

BACKGROUND ART

Various gene therapy approaches have been developed as alternatives to traditional protein therapy approaches. However, important challenges still remain in gene therapy. One of the major challenges of gene therapy is to achieve efficient influx of genes across plasma membranes (in animal cells) and nuclear membranes with minimal cytotoxicity.

Gene therapy systems can be broadly classified into viral vector-mediated systems and nonviral vector-mediated systems. Viral vectors are constructed using retroviruses or adenoviruses and have the advantage of high transfection efficiency into cells. However, viral vectors have problems associated with in vivo immunogenicity and suffer from inherent problems associated with genetic recombination. In attempts to overcome the stability problems of such viral vectors, various polymeric gene delivery systems have been developed as alternatives to traditional viral vector-based gene delivery strategies. For efficient gene delivery, polymeric vectors need to overcome intracellular trafficking barriers such as endosomal escape and nuclear localization.

Gene leakage occurs from synthetic peptide-based gene delivery systems in endosomal membranes at low pH, leading to DNA condensation and rapid endosomal escape. Accordingly, the use of synthetic peptide-based gene delivery systems can overcome the problems encountered with polymeric gene delivery systems.

For such reasons, a variety of synthetic peptides have been developed to promote in vitro gene delivery into several cell lines. However, these synthetic peptides also suffer from the problems of toxicity and serum instability in in vivo applications. Particularly, in this regard, research is being conducted on vectors using short cationic peptides. Even in this case, there are some problems, such as unstable nucleic acids in extracellular spaces. Other problems of the vectors are poor stability of complexes with nucleic acids and low gene expression level.

Particularly, in the case of nucleic acid delivery for RNAi, the stability of complexes with nucleic acids is low, making it difficult to deliver the nucleic acids into synthetic peptides. In view of this, lipids, liposomes, etc. have been used for nucleic acid delivery but failed to achieve effective in vivo systemic circulation.

Thus, the present inventors have investigated gene delivery systems using peptides, and as a result, found that PEGylation of a vector having a nona-arginine (R9) structure in which cysteine (Cys) residues are attached to one or both termini of the R9 can markedly improve the in vivo delivery efficiency of siRNA. The present invention has been accomplished based on this finding.

DETAILED DESCRIPTION OF THE INVENTION

Problems to be Solved by the Invention

A principal object of the present invention is to provide a siRNA delivery system containing polyethylene glycol (PEG) and a nona-arginine (R9) peptide, and a method for in vivo delivery of the siRNA delivery system by systemic administration.

A further object of the present invention is to provide a complex containing the siRNA delivery system and a desired siRNA.

Another object of the present invention is to provide various applications of the complex.

Means for Solving the Problems

Aspects of the present invention provide various applications of a siRNA delivery system for systemic circulation based on polyethylene glycol (PEG) and a nona-arginine (R9) peptide. Particularly, the present invention is directed to an effective method for in vivo delivery of siRNA by systemic administration to treat a target disease.

One embodiment of the present invention provides a siRNA delivery system (PEG-R9) for systemic circulation containing polyethylene glycol (PEG) and a nona-arginine (R9) peptide.

Other embodiments of the present invention provide a complex (PEG-R9-siRNA) for systemic circulation containing polyethylene glycol (PEG), a nona-arginine (R9) peptide, and siRNA for the treatment of a target disease, and a pharmaceutical composition for systemic circulation containing the complex.

Particularly, Cys residues are attached to one or both termini of R9. The nona-arginine (R9) peptide preferably has a Cys-(D-R9)-Cys or Gly-(D-R9)-Cys structure, more preferably a Cys-(D-R9)-Cys structure.

The delivery system has a structure in which PEG molecules are attached to one or both termini of the peptide through the amine ($-NH_2$) groups of the Cys residues.

Preferably, the polyethylene glycol (PEG) has a molecular weight of 500 daltons.

The complex for systemic circulation according to the present invention has a diameter of 200 nm or less, thus being suitable for siRNA delivery. The complex of the present invention has a charge ratio (+/−) of 6:1 to 15:1, ensuring high transfection efficiency. The highest transfection efficiency of the complex is obtained in a charge ratio (+/−) of 12:1.

The complex of the present invention can extend the in vivo circulation time of siRNA for the treatment of a target disease, thus being very effective in treating the disease.

In one embodiment of the present invention, the siRNA is siVEGF as a gene for cancer therapy.

The PEG-R9-siRNA of the present invention can be used as an effective siRNA delivery system for in vivo systemic circulation due to its high transfection efficiency, low cytotoxicity, and high expression efficiency of the target gene.

Effects of the Invention

Particularly, the PEG-R9 of the present invention can provide a base for a siRNA delivery system that is capable of significantly increasing the in vivo delivery efficiency of siRNA by systemic administration. The PEG-R9 of the present invention uses a nona-arginine (R9) structure, as a protein transduction domain, in which Cys residues are attached to one or both termini of R9. PEGylation of one or both termini of the R9 structure contributes to a considerable improvement in the systemic delivery efficiency of siRNA. Therefore, the PEG-R9 of the present invention is very useful as a siRNA delivery system for effective systemic administration.

MODE FOR CARRYING OUT THE INVENTION

Figure 1:
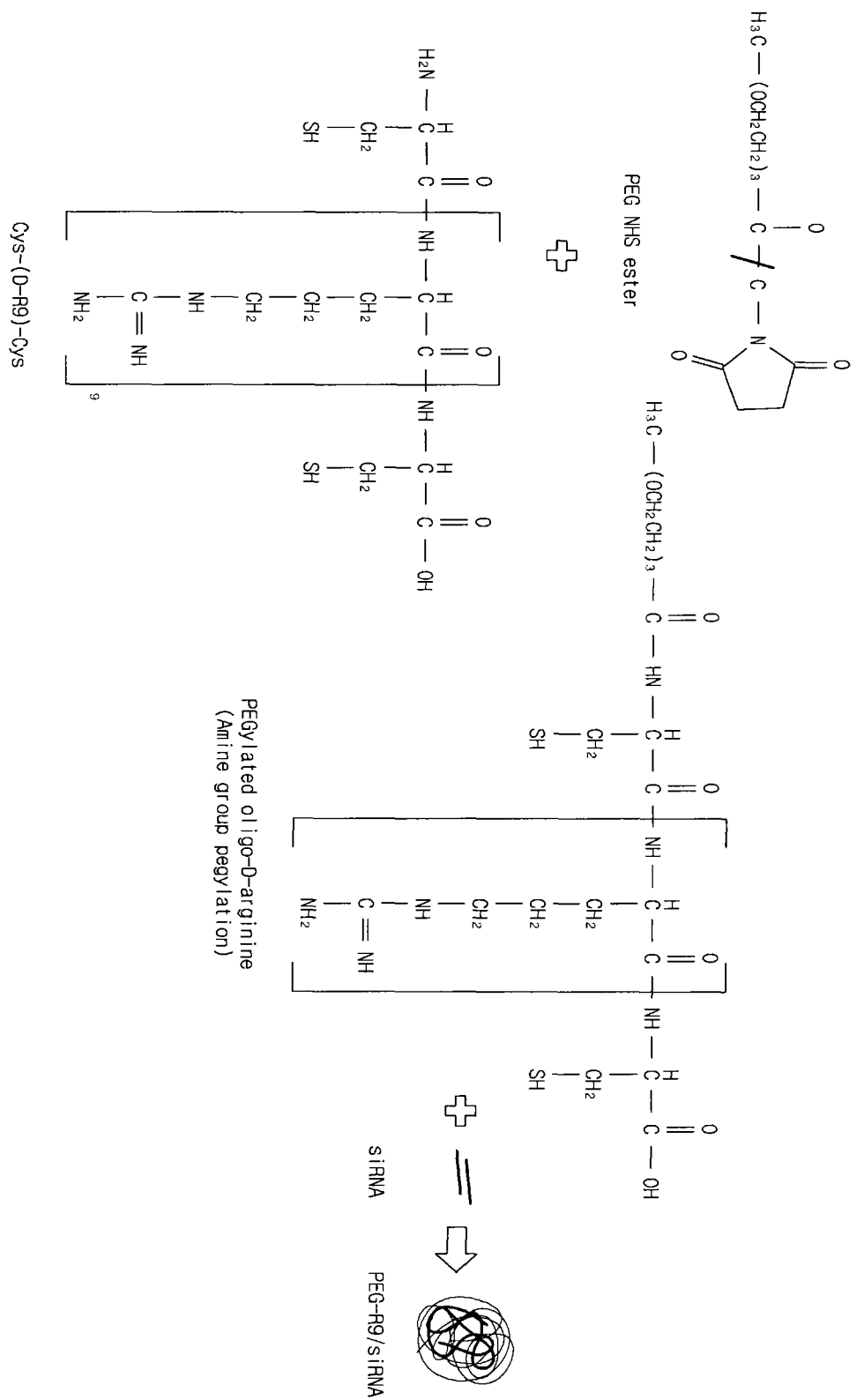
FIG. 1 is a schematic diagram showing a scheme for the synthesis of a nucleic acid delivery system using a polyethylene glycol (PEG)/oligoarginine (R9) conjugate.

The definitions of the terms used herein are as follows

By "gene" is meant any nucleic acid sequence or portion thereof with a functional role in encoding or transcribing a protein or regulating other gene expression. The gene may consist of all the nucleic acids responsible for encoding a functional protein or only a portion of the nucleic acids responsible for encoding or expressing a protein. The nucleic acid sequence may contain a genetic abnormality within exons, introns, initiation or termination regions, promoter sequences, other regulatory sequences or unique adjacent regions to the gene.

The term "polynucleotide" refers to a polymeric form of nucleotides of any length, such as deoxyribonucleotides as well as ribonucleotides.

By "nucleic acid" is meant to include any DNA or RNA, for example, chromosomal, mitochondrial, viral and/or bacterial nucleic acid present in tissue sample. The term "nucleic acid" encompasses either or both strands of a double stranded nucleic acid molecule and includes any fragment or portion of an intact nucleic acid molecule. A representative target nucleic acid used in the present invention is siRNA.

The term "vector" refers to a nucleic acid molecule capable of transporting another nucleic acid to which it has been linked. The term "expression vector" is intended to include a plasmid, cosmid or phage, which can synthesize a protein encoded by a recombinant gene carried by the vector.

A preferred vector is a vector that can self-replicate and express a nucleic acid bound thereto.

By "transfection" is meant a process by which a nucleic acid (e.g., DNA or RNA) is directly introduced into an animal culture cell to express its genetic traits. Generally, a target gene is contained in a carrier, such as a plasmid, and introduced into the nucleic acid. In many cases, the introduced gene is inserted into a chromosome when stabilized in the cell. The cell into which the nucleic acid has been introduced is called a "transductant". Several processes have been developed to overcome the problem of low transduction efficiency. Examples of such processes include calcium phosphate co-precipitation, DEAE-dextran treatment, electroporation, and redistribution (fusion of artificial membranes called liposomes with cells for DNA complexation).

By "zeta potential" is meant the electrokinetic potential arising from a density gradient of positive charges in a diffuse double layer of immobile water attached to the surface of a charged particle and mobile water easily detachable from the particle. Zeta potential is also expressed as an electrical potential difference between cell surface and surrounding culture fluid.

By the term "charge ratio" in a complex that functions as a gene delivery system, it is meant the ratio of the quantity of charges of a support or carrier to that of charges of DNA when the negatively charged DNA is bound to the positively charged support or carrier by an electrostatic attractive force. When the complex is positively charged as a whole, good delivery efficiency is attained, which is explained by the fact that the cell membrane is negatively charged.

The terms "amino acid" and "amino acid residue" are intended to include natural amino acids, unnatural amino acids, and modified amino acids. Unless otherwise stated, all mentions about amino acids include general mentions about the amino acids and specific mentions about both D- and L-stereoisomers of the amino acids (so long as their structures allow such stereoisomeric forms) according to their names. Examples of the natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). The D isomer of arginine (Arg) is preferably used in the present invention.

The term "gene expression" generally refers to the cellular processes by which a biologically active polypeptide is produced from a DNA sequence and exhibits a biological activity in a cell. As such, gene expression involves not only transcription and translation processes, but also involves post-transcriptional and post-translational processes that can influence a biological activity of a gene or gene product. These processes include, but are not limited to RNA syntheses, processing, and transport, as well as polypeptide synthesis, transport, and post-translational modification of polypeptides.

"Luciferase" is an enzyme that catalyzes the oxidation of luciferin to convert chemical energy into light energy, achieving light emission. Luciferase functions like a reporter gene whose in vivo expression is continuously measured in real time and whose effect on a target material can be verified. Luciferase is obtainable directly from the bodies of insects such as fireflies or glow-worms. Alternatively, luciferase may be obtained by expression in a microorganism including a recombinant DNA fragment encoding the enzyme.

The term "support or carrier" refers collectively to polymeric materials responsible for carrier transport when active materials are present in a bound form with other materials in organisms or materials migrate through cell membranes. Non-limiting examples of supports suitable for use in the present invention include: buffers, such as phosphate, citrate, and other organic acids; antioxidants, such as ascorbic acid; low molecular weight (less than about 10 residues) polypeptides; proteins, such as serum albumin, gelatin or immunoglobulins; hydrophilic polymers, such as polyvinylpyrrolidone; amino acids, such as glycine, glutamine, asparagine, arginine or lysine; other carbohydrates, such as monosaccharides, disaccharides, glucose, mannose, and dextrins; chelating agents, such as EDTA; sugar alcohols, such as mannitol and sorbitol; salt-forming counterions, such as sodium; and/or nonionic surfactants, such as TWEEN®, polyethylene glycol (PEG), and PLURONICS®.

"Treatment" is an approach to obtain beneficial or desired results, including clinical results. "Treatment" or "alleviation" of a disease, a disorder or a condition means that the extent of the condition, disorder or disease and/or undesired clinical symptoms is reduced and/or the progression of the condition, disorder or disease is retarded or prolonged, compared to when the condition, disorder or disease is not treated. For the purposes of the present invention, beneficial or desired results can include, but are not limited to, relief or amelioration of one or more symptoms, diminishment of extent of disease, stabilized (i.e. not worsening) state of disease, delay or slowing of disease progression, amelioration or alleviation of disease state, and remission (whether partial or total), whether detectable or undetectable. "Treatment" can also mean prolonged survival compared to expected survival when no treatment is received. "Treatment" is not necessarily limited by administration of a single dose and is often effected by administration of a series of doses. Thus, a therapeutically effective amount, an amount sufficient to alleviate or an amount sufficient to treat a disease, disorder or condition can be administered once or more.

The term "disorder" is any condition that would benefit from treatment with molecules identified using a transgenic animal model. This includes chronic and acute diseases or illness including pathological conditions that predispose mammals to diseases in question. Non-limiting examples of diseases to be treated herein include cancers.

By "therapeutically effective amount" is meant the amount of an active compound in a composition that will elicit the biological or medical response (including relief of symptoms of a disorder to be treated) of a tissue, system, subject or human in need thereof that is being sought by a researcher, veterinarian, medical doctor or other clinician.

The term "gene therapy" refers to the treatment of a genetic disease by modifying a mutated gene or the treatment of a disease by regulating protein expression using a gene or RNAi. That is, gene therapy is a process for the treatment of a disease by transplanting an exogenous normal gene into the cell of a patient to change the phenotype of the cell.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "include (comprise)," "includes (comprises)," and "including (comprising)" will be understood to imply the inclusion of a stated step or element or group of steps or elements but not the exclusion of any other step or element or group of steps or elements.

The present invention will now be described in detail.

The present invention is directed to intracellular delivery (transfection) of a nucleic acid, and particularly to various applications including a delivery system and method for enhancing the in vivo delivery efficiency of siRNA by systemic administration.

Aspects of the present invention are directed to a non-viral siRNA delivery system or vector for systemic circulation including polyethylene glycol (PEG) and a poly(oligo-arginine), particularly a nona-arginine (R9) peptide, and a method of using the same.

The non-viral gene delivery vector refers collectively to carriers that transfer genes into cells without using viruses. Representative examples of such non-viral gene delivery vectors are vectors that coat nucleic acids based on the electrical interaction between cationic sites on the vectors and anionic sites on the negatively charged nucleic acids constituting genes.

The poly(oligo-arginine) includes a poly(oligo-L-arginine) and a poly(oligo-D-arginine), most preferably a poly(oligo-D-arginine). A high molecular weight poly(oligo-D-arginine) effectively promotes the condensation of DNA to form a stable complex and internalizes the DNA into a cell. After internalization, the complex escapes from an endosome to the cytoplasmic space by the reduction of disulfide bonds.

The reducible poly(oligo-D-arginine) preferably consists of cationic oligomers, each of which includes cysteine residues cross-linked by a disulfide bond at the terminal positions, but is not limited thereto. Cysteine is the only amino acid that contains a sulfhydryl group capable of cross-linking with an adjacent cysteine molecule to form a disulfide. The protein transduction domain (PTD) portions other than the cysteine residues cross-linked by disulfide bonds may become any cationic peptides.

More preferably, the reducible poly(oligo-D-arginine) has a structure in which Cys residues are attached to one or both termini of each oligo-D-arginine. Most preferably, Cys residues are attached to both termini of each cationic oligo-D-arginine. For example, the reducible poly(oligo-D-arginine) may consist of Cys-(D-R9)-Cys or Gly-(D-R9)-Cys repeating units. The reducible poly(oligo-D-arginine) may be prepared by DMSO oxidation of the terminal cysteine-thiol groups of the Cys-(D-R9)-Cys or Gly-(D-R9)-Cys repeating units. The reducible poly(oligo-D-arginine) may be cleaved into Cys-(D-R9)-Cys fragments by treatment with a reducing agent.

That is, the reducible poly(oligo-arginine) has a structure in which Cys residues are attached to one or both termini of nona-arginine (R9), preferably a Cys-(D-R9)-Cys or Gly-(D-R9)-Cys structure, most preferably a Cys-(D-R9)-Cys structure. The presence of Cys residues at both terminal positions enables effective condensation of an oligopeptide complex (peptoplex) and allows the resulting complex to have neutral charge characteristics.

The gene delivery system of the present invention is designed for systemic circulation and includes a nona-arginine (R9) structure and polyethylene glycol (PEG) attached to the R9 structure. In the nona-arginine (R9) structure, Cys residues are attached to one or both termini of R9.

Herein, the delivery system of the present invention is also abbreviated as "PEG-R9". That is, the PEG-R9 of the present invention refers to a structure in which polyethylene glycol (PEG) molecules are attached to one or both termini of the R9 structure. Cys was separately shown in experiments conducted to investigate the binding effect of Cys in Comparative Example 1 that follows.

Protein PEGylation is a process used to improve the systemic circulation efficiency of target genes. Proteins usually undergo fusion reactions, called carboxyl PEGylation, amine PEGylation, N-terminal PEGylation, and thiol PEGylation, via four functional groups.

The delivery system of the present invention is based on the R9 peptide structure in which Cys residues are attached to one or both termini of R9, for example, a Cys-(D-R9)-Cys or Gly-(D-R9)-Cys peptide structure, and is prepared by amine PEGylation of Cys.

The PEG-R9 vector of the present invention is efficient in in vivo nucleic acid delivery, particularly in vivo siRNA delivery.

RNA interference (RNAi) is a natural mechanism including specifically downregulating the expression of target genes by double-stranded short interfering RNA (siRNA). Various types of RNAi-mediating agents are known and examples thereof include short interfering RNA (siRNA), microRNA (miRNA), and small hairpin RNA (shRNA). The PEG-R9 vector of the present invention is particularly preferred for in vivo delivery of short interfering RNA (siRNA).

Liposomes have been used for in vivo siRNA delivery. Like other particulate drug delivery systems for systemic circulation, liposomes tend to be lost in the circulatory system by phagocytosis of macrophages mainly present in the liver and spleen due to the adsorption of blood proteins. Another problem is that drugs are released from liposomes during circulation in blood. In attempts to solve such problems, many techniques have been developed, particularly based on the fact that phagocytosis of macrophages occurs through the adsorption of opsonin proteins on the liposome surface. For example, liposomes were developed that use phospholipid-PEG derivatives, as constituents, in which phospholipids are terminated with polyethylene glycol (PEG) or whose surface is coated with PEG or polysaccharides to suppress the adsorption of opsonin proteins.

However, the use of such phospholipid-PEG derivatives as constituents of liposomes deteriorates the stability of the liposomes per se and causes low transfection efficiency and severe toxicity, making in vivo application of the liposomes difficult for in vivo administration. Most of the liposomes are delivered to the liver after administration and are more distributed in the liver than in tumor.

In contrast, the PEG-R9, most preferably PEG-Cys-R9-Cys, structure of the present invention is very effective in the systemic circulation of siRNA without causing the above problems.

Other aspects of the present invention are directed to a complex for siRNA delivery for systemic circulation including polyethylene glycol (PEG), a nona-arginine (R9) peptide, and a siRNA, and a composition for treating a target disease including the complex. The siRNA as a target gene is bound to the gene delivery system. Preferably, the R9 peptide includes Cys residues attached to one or both termini of R9.

The siRNA as a gene to be delivered by the complex of the present invention may be any of those that can be inserted for the treatment of a target disease. They may be either naturally occurring or artificially synthesized and may exist in various sizes from oligonucleotides to chromosomes. These genes originate from various sources, such as humans, animals, plants, bacteria, and viruses and can be acquired by any suitable method known in the art.

The complex of the present invention may include gene expression regulatory factors for the treatment of a target disease, such as cancer, for example, transcription promoters, enhancers, silencers, operators, terminators, attenuators, and other expression regulatory factors.

One embodiment of the present invention provides a composition for treating a target disease including the complex for siRNA delivery.

In some embodiments, the siRNA is expressed from transcription units inserted into the nucleic acid vector (also referred to generally as "recombination vector" or "expression vector"). The intracellular delivery of nucleic acid molecules encoding the siRNA using a vector enables targeting of the specific gene.

Many other suitable methods are known in the art. Generally, transfection into cells expressing target genes may be performed by various methods, for example, electroporation and the use of cationic lipids or cationic polymers as helpers. Thereafter, the transfected cells are cultured under conditions suitable for the expression of a target gene. Subsequently, the expression of the target gene is determined by any suitable technique, for example, RT-PCR or quantitative measurement of a reporter gene. Basically, any type of cells may be used for transfection/transformation. In a preferred embodiment, the cells are eukaryotic cells, preferably animal cells, more preferably mammalian cells, most preferably human cells.

In one embodiment of the present invention, the siRNA is siVEGF for anticancer use.

Vascular endothelial growth factors (VEGFs) are factors overexpressed in most cancer (tumor) cells, such as thyroid cancer, breast cancer, prostate cancer, colon cancer, and uterine cervical cancer. VEGFs are highly involved in the development, recurrence, and metastasis of cancer. Therefore, the PEG-R9 delivery system of the present invention is suitable for anticancer therapy due to its ability to efficiently deliver siVEGF into cancer cells.

The PEG-R9 delivery system of the present invention is useful for the treatment of VEGF-overexpressing cancers, for example, lung cancer, gynaecological malignancy, melanoma, breast cancer, pancreatic cancer, ovarian cancer, uterine cancer, colorectal cancer, prostate cancer, renal cancer, head cancer, pancreatic cancer, liver cancer (hapatocellular cancer), uterine cancer, neck cancer, renal cancer (renal cell carcinoma), sarcoma, myeloma, and lymphoma.

A therapeutically effective amount of the complex or composition according to the present invention can be provided by any route of administration known in the art. The embodiment of the present invention is applied such that the PEG-R9-siVEGF can be transfected into cancer cells.

The composition of the present invention may include or use any of the above means for transfecting genetic materials into target cells but is not limited thereto. The composition of the present invention may further include a cationic or amphiphilic material to release the siRNA into cancer cells.

The nucleic acid molecules and a promoter may also be prepared into pharmaceutical formulations according to suitable pharmaceutical synthesis techniques known in the art.

The composition of the present invention may include an active ingredient or a pharmaceutically acceptable salt thereof. The composition may be administered batchwise or continuously. The composition may include one or more pharmaceutically acceptable additives well known in the art, in addition to the active ingredient. Examples of such additives include excipients, vehicles, buffers, and stabilizers. The additives should be non-toxic and should not interfere with the efficacy of the active ingredient.

The vehicles may take various forms depending on formulations suitable for administration, for example, topical, intravenous, oral, cerebral, epineurial or parenteral administration. The composition of the present invention can be prepared for oral or parenteral administration by mixing with generally used diluents and excipients, such as fillers, extenders, binders, wetting agents, disintegrating agents, and surfactants.

Effective doses and dosage regimes for the administration of the complex and the composition including the complex can be empirically determined by those skilled in the art. Each of the complex and the composition can be administered in either single or multiple doses.

The PEG-R9-based delivery system and complex for in vivo systemic circulation of siRNA according to the present invention have the following advantages:

(1) The "PEG-R9" of the present invention readily forms a conjugate with siRNA and very effectively protects the siRNA.

The PEG-R9 of the present invention is effective in condensing siRNA in a charge ratio of ≥6:1. The charge ratio (+/−) of the PEG-R9 is preferably limited to the range of 6:1 to 15:1, more preferably 9:1 to 15:1. Within this range, high transfection efficiency of the PEG-R9 is attained. In one particular embodiment, the delivery system of the present invention shows the highest gene transfection efficiency in a charge ratio of 12:1.

The charge ratio refers to the ratio of the positively charged arginine constituting the delivery system to the negatively charged phosphate groups constituting the gene (nucleic acid). In the present invention, the negatively charged gene is allowed to react with a 6- to 15-fold excess of the delivery system. That is, the charge ratio of 6:1 to 15:1 indicates that the amount of the delivery system is 6 to 15 times larger than that of the target gene.

High delivery efficiency is obtained when the gene delivery complex is positively charged as a whole because cell membranes are negatively charged. The positively charged complex can easily pass through cell membranes by charge-to-charge interaction. If the complex is negatively charged, it does not readily cross cell membranes. The quantity of electric charges of the complex affects the ability of the complex to cross cell membranes. A larger quantity of electric charges indicates a better ability to cross cell membranes.

The PEG-R9 of the present invention has much higher gene expression efficiency than cationic polyethylenimine (PEI) supports generally used in the art. That is, the PEG-R9 exhibits the ability to more effectively condense siRNA and protects DNA from degradation in serum in the optimum charge ratio defined above.

(2) The PEG-R9 of the present invention binds to siRNA to form a nano-sized complex and has a positive zeta potential value.

When the PEG-R9 is bound to siRNA, it more effectively condenses DNA by electrostatic interaction. The PEG-R9 of the present invention bears a positive charge under neutral conditions due to the presence of Cys residues attached to one or both termini of R9. This enables effective concentration of the complex to a nanometer size (ca. ≤200 nm) and allows the complex to have a positive zeta potential in a charge ratio of ≥5.

As explained earlier, the positively charged complex can easily pass through cell membranes by charge-to-charge interaction. If the complex is negatively charged, it does not readily cross negatively charged cell membranes. Accordingly, the positive zeta potential value of the complex suggests high gene delivery efficiency of the complex.

Particularly, the PEG-bound complex has a smaller particle size than a PEG-unbound complex and the complex including cysteine (Cys) residues attached to both termini of R9 has a smaller particle size and a more uniform size distribution, which were confirmed in the Examples Section that follows. That is, according to the most preferred construction of the complex, cysteine residues are attached to both termini of the R9 oligopeptide and PEG is attached thereto.

(3) The PEG-R9 of the present invention has high intracellular siRNA delivery efficiency and expression rate and causes no cytotoxicity.

Figure 5:
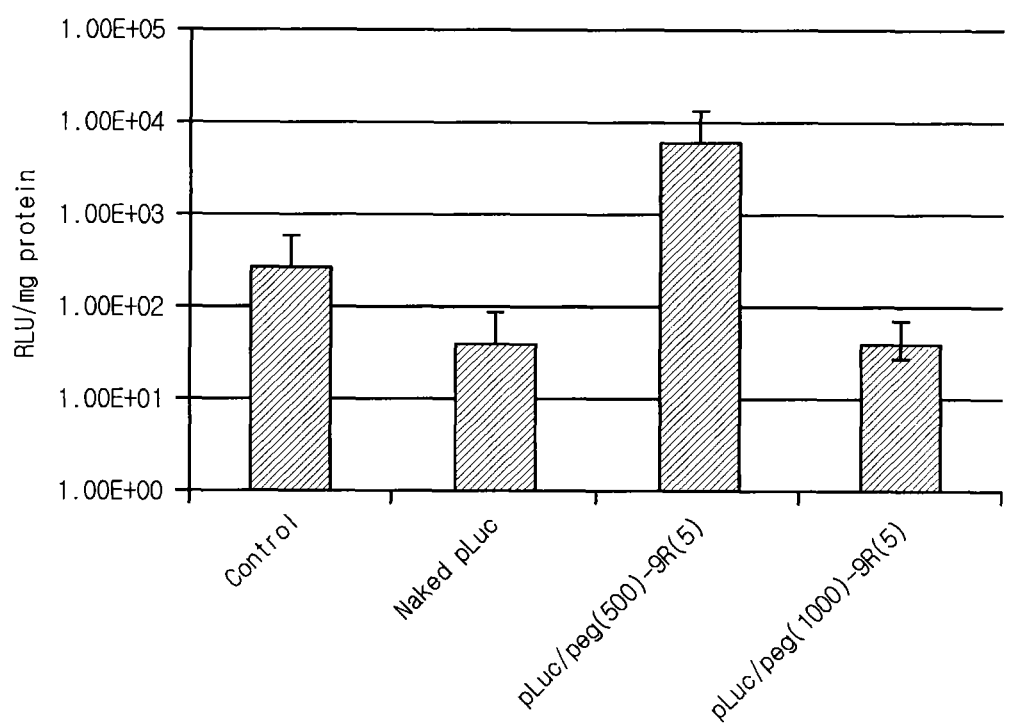
FIG. 5 shows the results of luciferase assay using PEG500 and PEG1000 to find an optimum PEG molecular weight.

In comparison with TAT as a gene delivery system, the PEG-R9 of the present invention in which Cys residues are attached to R9 and PEG is attached thereto was confirmed to have high siRNA delivery efficiency (FIG. 8) and high intracellular expression rate of luciferase DNA (FIG. 5).

Figure 6:
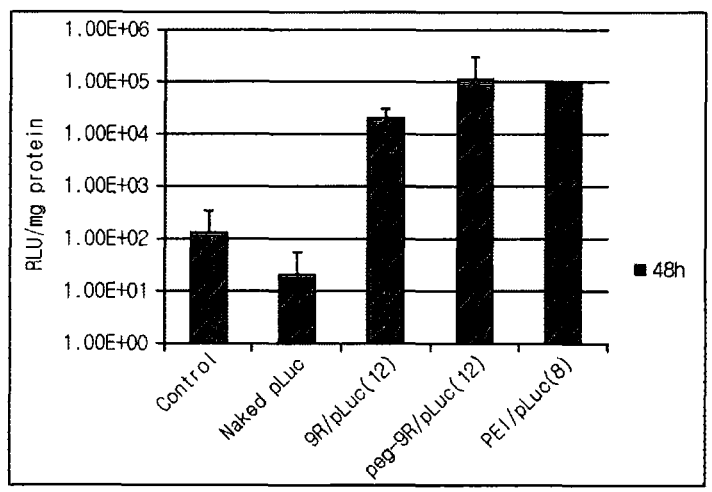
FIG. 6 shows the results of (a) luciferase assay for intracellular gene delivery efficiency and (b) MTT assay for cytotoxicity.
Figure 6:
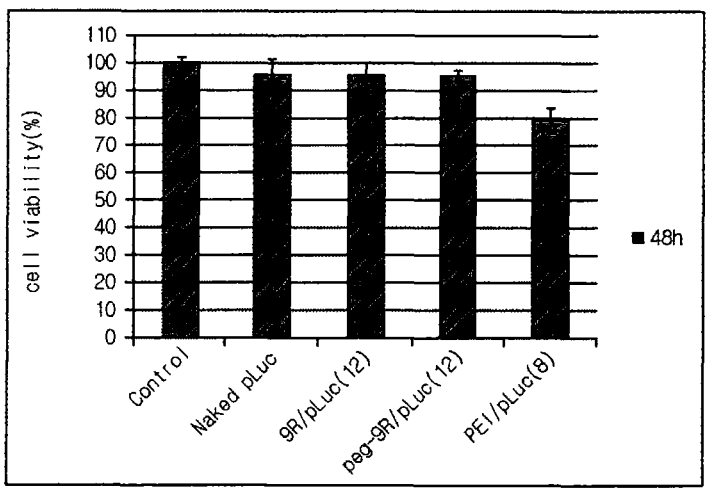

In comparison with a PEI support as a general cationic polymer support, the PEG-R9 of the present invention has low cytotoxicity, thus being suitable for in vivo use. In the Examples Section that follows, the PEG-R9 showed a cell viability of at least 95% whereas the PEI support showed toxicity (FIG. 6).

(4) The PEG-R9 of the present invention extends the in vivo circulation time of siRNA, suggesting its superior anticancer effect.

In the Examples Section that follows, the PEG-R9/siRNA conjugate was observed to significantly inhibit the growth of cancer cells after intravenous injection into nude mice.

To sum up, the PEG-R9 and the PEG-R9-siRNA of the present invention have high transfection efficiency, low cytotoxicity, and high expression efficiency of the target gene, thus being suitable for use as effective siRNA delivery systems for systemic circulation.

EXAMPLES

The present invention will be explained in more detail with reference to the following examples. However, it will be obvious to those skilled in the art that these examples are provided for illustrative purposes and are not construed as limiting the scope of the invention.

Example 1: Formation of PEG-R9-siRNA Complex

FIG. 1 is a schematic diagram showing a scheme for the synthesis of a nucleic acid delivery system using a polyethylene glycol/oligoarginine conjugate.

As shown in FIG. 1, N-hydroxysuccinimide (NHS) ester PEG (molecular weight 500, Thermo Fisher Scientific Inc. Rockford, Ill. USA) is attached to the amine group (—NH$_2$) of one of the Cys residues of the Cys-(D-R9)-Cys structure. Under weakly basic conditions (pH ca. 7-8), the peptide was allowed to react with NHS ester PEG in a ratio of 1:1 to form a peptide bond.

siVEGF (5-AUGUGAAUGCAGACCAAAGAA dTdT-3) was purchased from Bioneer Corporation, Korea, and the peptide (PEG-Cys-(D-R9)-Cys) was ordered from Anygen Co., Ltd., Korea.

50 pmol of siVEGF, deionized water, and PEG-R9 (charge ratio: 6, 9) were allowed to stand at room temperature for 20 min to construct oligo-peptoplexes. Thereafter, the oligo-peptoplexes were subjected to electrophoresis at 100 V in 2% agarose gel for 20 min. After addition of 90 vol % of mouse serum, stability test was conducted up to 24 h. PEG-R9 was separated from siVEGF by heparin addition. It was confirmed whether the band of siVEGF was maintained.

Figure 2:
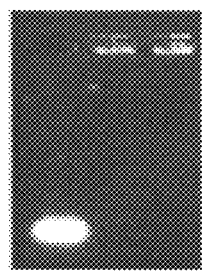
FIG. 2 shows images confirming the formation and stability of PEG-R9-siVEGF polyplexes.
Figure 2:
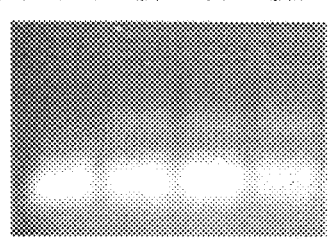

As a result, PEG-R9 readily formed polyplexes with the nucleic acid and effectively protected the nucleic acid against the serum, as shown in FIG. 2.

Example 2: Sizes and Zeta Potentials of the PEG-R9-siRNA Polyplexes

In this example, the zeta potentials and mean diameters of the PEG-R9/siVEGF oligo-peptoplexes (complexes) were measured using dynamic light scattering (DLS).

Specifically, 5 μg of siVEGF, deionized water, and PEG-R9 (charge ratio: 6, 9, 12, 15) were allowed to stand at room temperature for 20 min to construct oligo-peptoplexes. The mean diameters and surface zeta potentials of the oligo-peptoplexes were measured using DLS equipped with a Zetasizer-Nano ZS (Malvern Instruments, UK).

Figure 3:
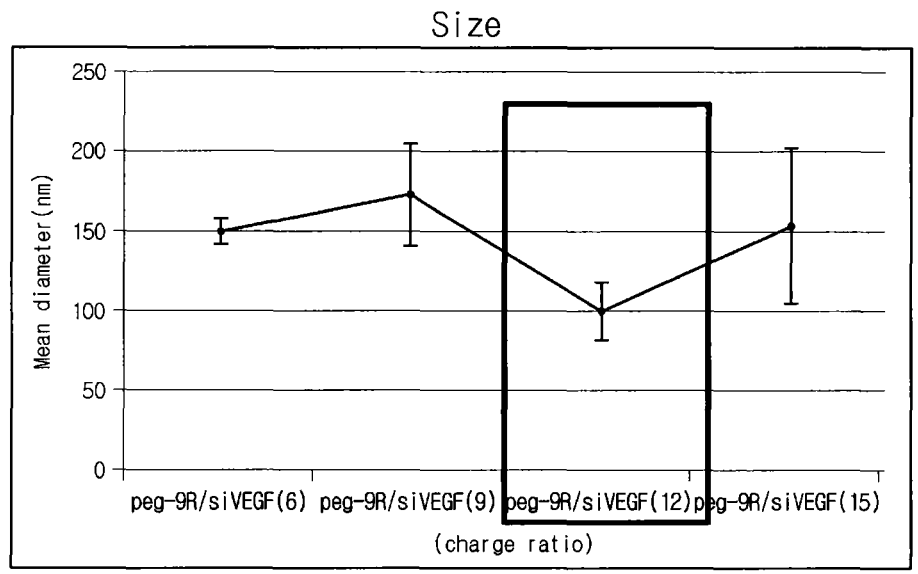
FIG. 3 shows the sizes and zeta potentials of PEG-R9-siVEGF polyplexes.
Figure 3:
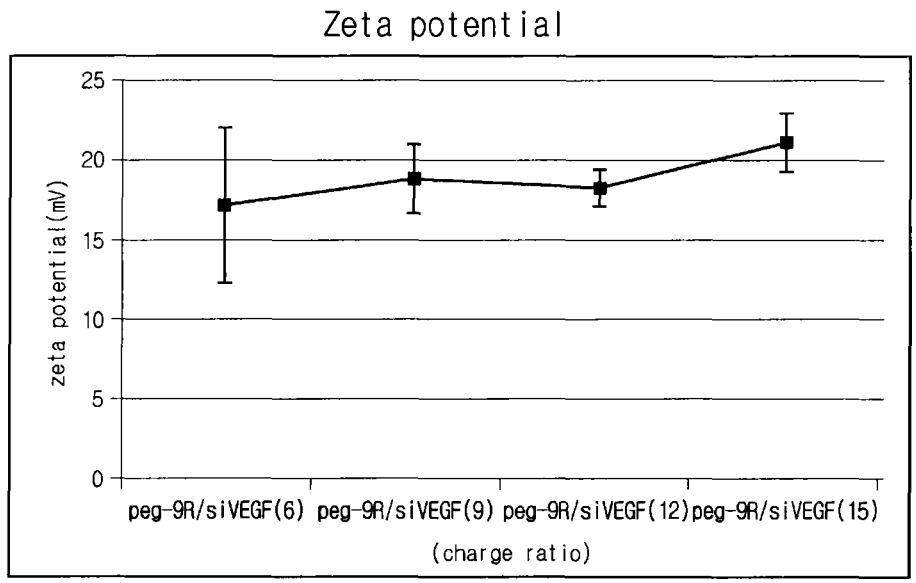

As shown in FIG. 3, the oligo-peptoplexes showed positive zeta potential values and mean diameters of less than 200 nm in charge ratios of 6 or more. The smallest mean diameter (100 nm) was observed in a charge ratio of 12.

Example 3: Evaluation of Intracellular Delivery (Transfection) Efficiency of PEG-R9

In the PEG-R9 structure, PEG was attached to C-(D-R9)-C. To confirm whether the C-(D-R9)-C structure was optimum, the C-(D-R9)-C structure was compared with G-(D-R9)-G, G-(D-R9)-C, and C-(D-R9)-G structures. Each of the G-(D-R9)-G, G-(D-R9)-C, C-(D-R9)-G, and C-(D-R9)-C delivery systems formed complexes with luciferase DNA in a charge ratio of 1:5. The intracellular transfection efficiencies of the complexes into cells were evaluated.

Figure 4:
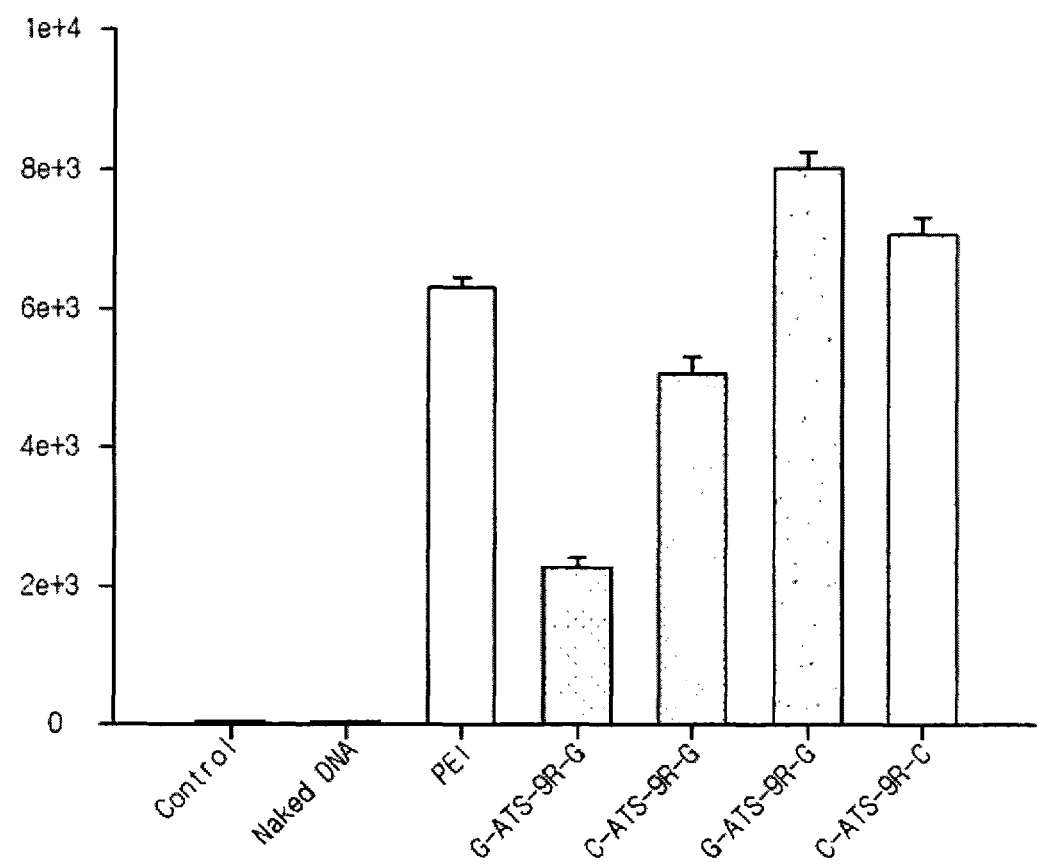
FIG. 4 is a graph comparing the transfection efficiency of a PEG-R9 delivery system including C-(D-R9)-C with the transfection efficiencies of PEG-R9 delivery systems including other D-R9 structures.

The results are shown in FIG. 4.

The complexes using the C-(D-R9)-G and C-(D-R9)-C structures showed high transfection efficiencies. The C-(D-R9)-C structure was selected for efficiency evaluation.

Example 4: Evaluation of Intracellular Delivery (Transfection) Efficiency of PEG-R9

In this example, the intracellular permeability of PEG-R9/FITC-siVEGF was evaluated by flow cytometry (FACS). FITC-siVEGF was purchased from Bioneer Corporation, Korea.

First, differentiation of squamous cell carcinoma (SCC7) cells purchased from ATCC was induced. The SCC7 cells were cultured in a complete medium supplemented with RPMI 1640 containing 10% FBS, 1% penicillin, and streptomycin at 37° C. in a 5% $CO_2$ atmosphere. The cells were subcultured three times a week.

The cultured SCC7 cells were seeded onto 12-well plate at a density of $1 \times 10^5$ cells/well. 24 h after seeding, complexes of 100 pmol of FITC-siVEGF and PEG-R9 (charge ratio: 8, 15, 23) were formed, followed by transfection. PEI complexes in a charge ratio of 8 were used as control. After 4-h incubation, the cells was washed with PBS, treated with trypsin, transferred to a 1.5 ml microtube, centrifuged at 1,300 rpm for 3 min, and washed with a fluorescence activated cell sorter (FACS) buffer. The intracellular delivery efficiency of PEG-R9/FITC-siVEGF was evaluated by FACS.

The results are shown in Table 1. As can be seen the results in Table 1, the intracellular delivery efficiency of PEG-R9/FITC-siVEGF was as high as PEI/FITC-siVEGF as the positive control.

TABLE 1

| | | | Transfection efficiency | | | |
|---|---|---|---|---|---|---|
| 4H | Naked Control | PEI/ FITC-siVGF | PEG-9R/ FITC-siVEGF | PEG-9R/ FITC-siVEGF (8) | PEG-9R/ FITC-siVEGF (15) | PEG-9R/ FITC-siVEGF (23) |
| % | 0.17 | 10.3 | 96.37 | 71.51 | 86.87 | 90.32 |

Example 5: Evaluation of Expression Efficiency and Toxicity of PEG-R9

In this example, luciferase gene expression was measured using a luciferase assay kit and cell viability was analyzed by MTT assay.

A luciferase assay kit was purchased from Promega (USA). A DC protein assay kit and a bovine serum albumin standard were purchased from Bio-Rad Laboratories (USA). SCC7 cells were seeded onto a 24-well plate at $2 \times 10^4$ cells/well. 24 h after seeding, the cells were transfected with plasmid luciferase (4 μg)/PEG-R9 complexes (charge ratio 12).

PEI complexes in a charge ratio of 8 were used as control. After 48-h incubation, the cells was washed with PBS and treated with 150 μl of a 1× cell lysis buffer reagent for 20 min. The cell lysate was obtained by scrapping, transferred to a 1.5 ml microtube, and centrifuged at 13,000 rpm for 3 min. The luminescence values of the cell lysate were measured using a 96-well plate photometer (Berthold Detection Systems, Germany) with a 20 s integration time and were expressed as relative luminescence units (RLU) per mg of cell protein.

Proteins were determined with the DC protein assay kit using the bovine serum albumin standard. Based on the above procedure, PEG500 and PEG1000 were compared to find which one would be most optimal.

The results are shown in FIG. 5. The intracellular transfection efficiencies of the complexes were evaluated. As a result, the complexes using PEG500 showed better gene delivery efficiency than the complexes using PEG 1000. PEG500 was used in this experiment.

Cell viability was measured by MTT [3-(4,5-dimethylthiazol-2-yl)-2,5-diphenyltetrazolium bromide] assay.

SCC7 cells were incubated in a 24-well plate and treated with R9, PEG-R9 complexes, and PEI complexes in the specified charge ratios. 48 h after transfection, 50 μl of MTT reagent and 500 μl of a medium were added to each well, followed by culture at 37° C. for 3 h. After removal of the culture media, 500 μl of dimethyl sulfoxide (DMSO) was added to each well, followed by culture at room temperature for 20 min. The absorbance was measured at 570 nm.

The results are shown in FIG. 6.

The intracellular gene delivery efficiencies were confirmed by luciferase assay. As a result, PEG-R9 was found to efficiently deliver the gene into the cells, where the gene was expressed. In addition, the cytotoxicity of PEG-R9 was much lower than the other gene delivery systems (e.g., PEI complexes).

Comparative Example 1: Identification of Optimum Delivery System for siRNA Delivery siVEGF was conjugated with different kinds of delivery systems. The sizes and zeta potentials of the conjugates were analyzed to find which delivery system would be optimal for siRNA delivery.

A group of cys-R9-cys, PEG-R9, and PEG-cys-R9-cys delivery systems and a group of PEG-cys-R9-cys, PEG-TAT, and PEG-cys-TAT-cys delivery systems were used, and their mean diameters were measured and compared.

Figure 7:
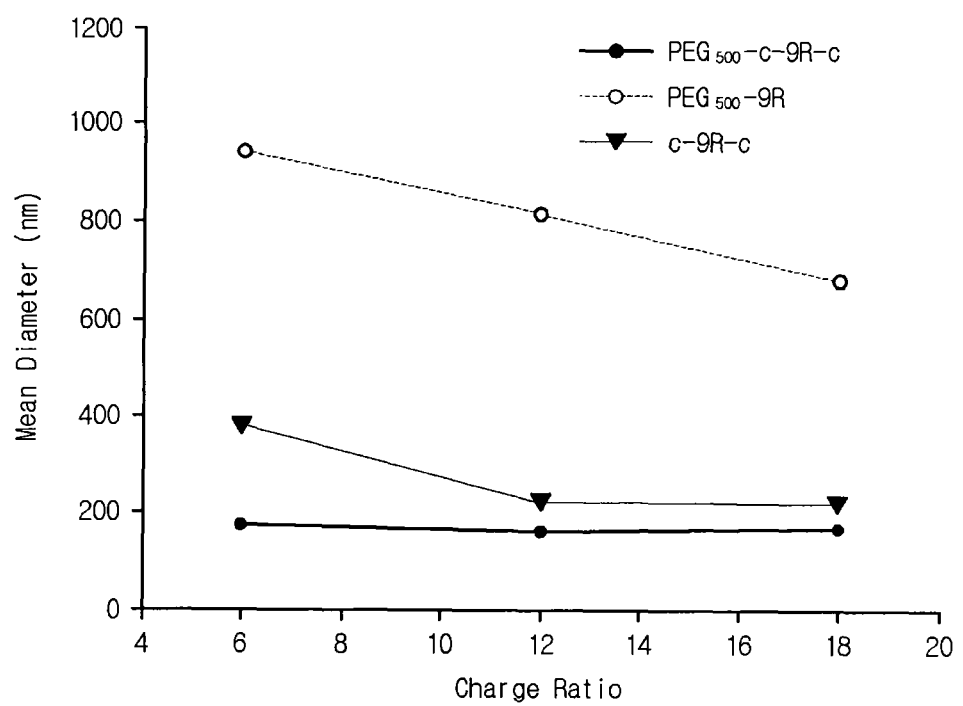
FIG. 7 shows the sizes and zeta potentials of delivery systems using cys-R9-cys, PEG-R9, and PEG-cys-R9-cys.
Figure 8:
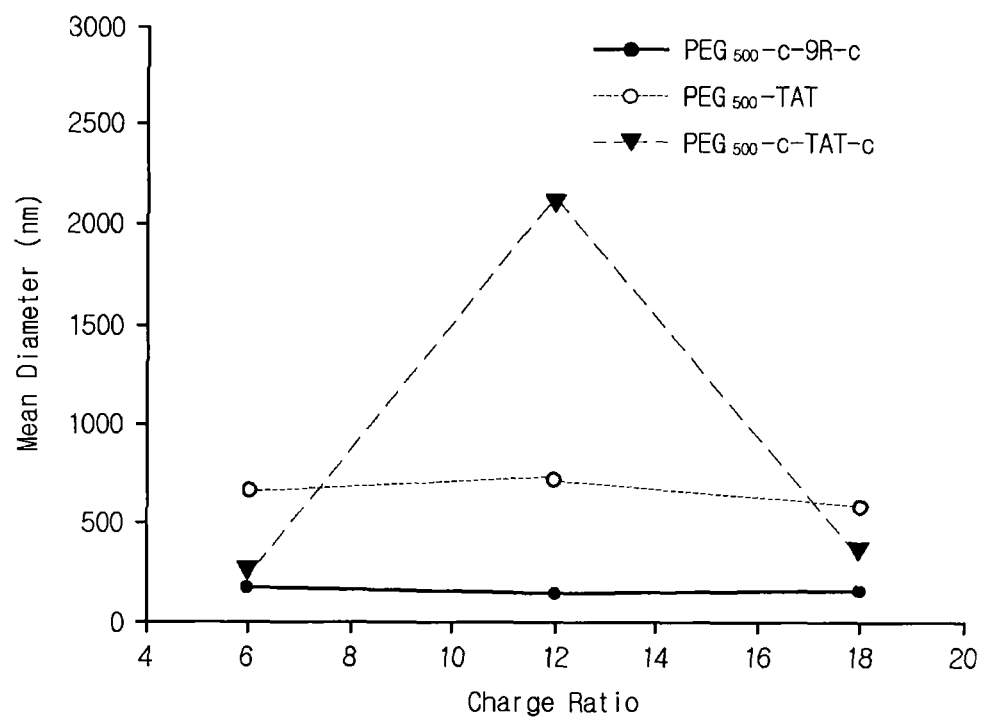
FIG. 8 shows the sizes and zeta potentials of delivery systems using PEG-cys-R9-cys, PEG-TAT, and PEG-cys-TAT-cys.

The results are shown in FIGS. 7 and 8.

It was confirmed that the PEG-bound delivery system containing cysteine residues at the termini of R9 were smaller and the delivery system containing no cysteine residues at the termini of R9 was rather larger in particle size than the PEG-unbound delivery system (FIG. 7). These results led to the conclusion that when cysteine residues were attached to both termini of R9 and PEG was attached thereto, the highest binding rate to siRNA was obtained.

The binding capacity of the TAT structure to the gene was compared with that of the R9 structure. As a result, the delivery system in which PEG was attached to the R9 structure was optimum for siRNA delivery than the delivery systems in which PEG was attached to the TAT structure (FIG. 8).

The above experimental results demonstrated that when cysteine residues were attached to the termini of R9 and PEG was attached thereto, the delivery system showed the most efficient binding to siRNA and its nanoparticles were also uniform in size.

Example 6: Anticancer Efficacy of PEG-R9-siVEGF $2 \times 10^6$ SCC7 cells were injected into the hind legs of 7 week old nude mice to induce cancer. Treatment did not begin until the tumor volume reached above 100 mm$^3$. siVEGF (10 µg)/PEG-R9 complexes, siVEGF (10 µg)/R9 complexes, and siVEGF (10 µg)/PEI complexes in the specified charge ratios were administered to the tail veins three times a week for two weeks. The nude mice were grouped (5 mice/group).

Figure 9:
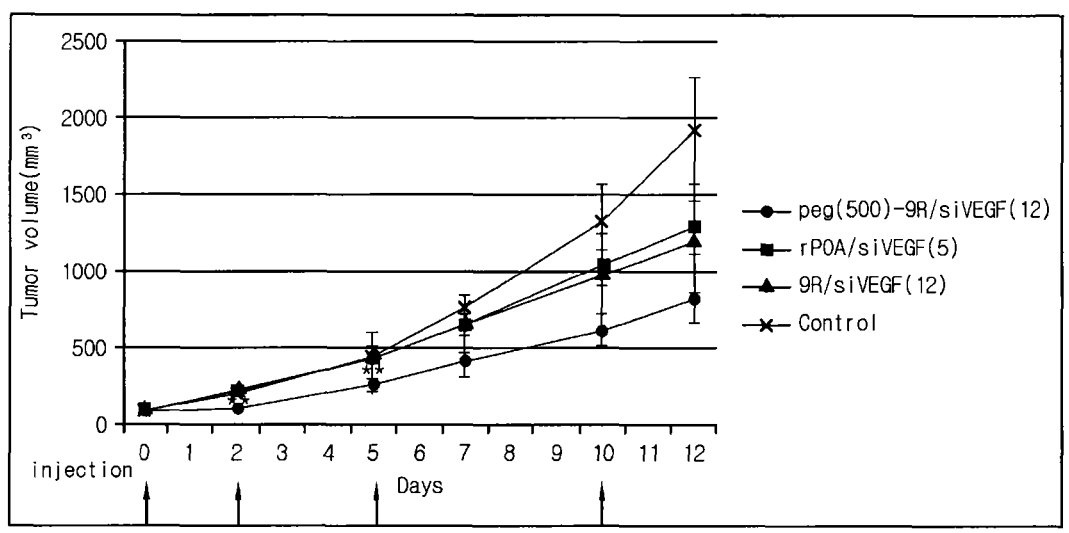
FIG. 9 is a graph comparing the growth rates of tumor cells after the administration of PEG-R9-siVEGF polyplexes.
Figure 10:
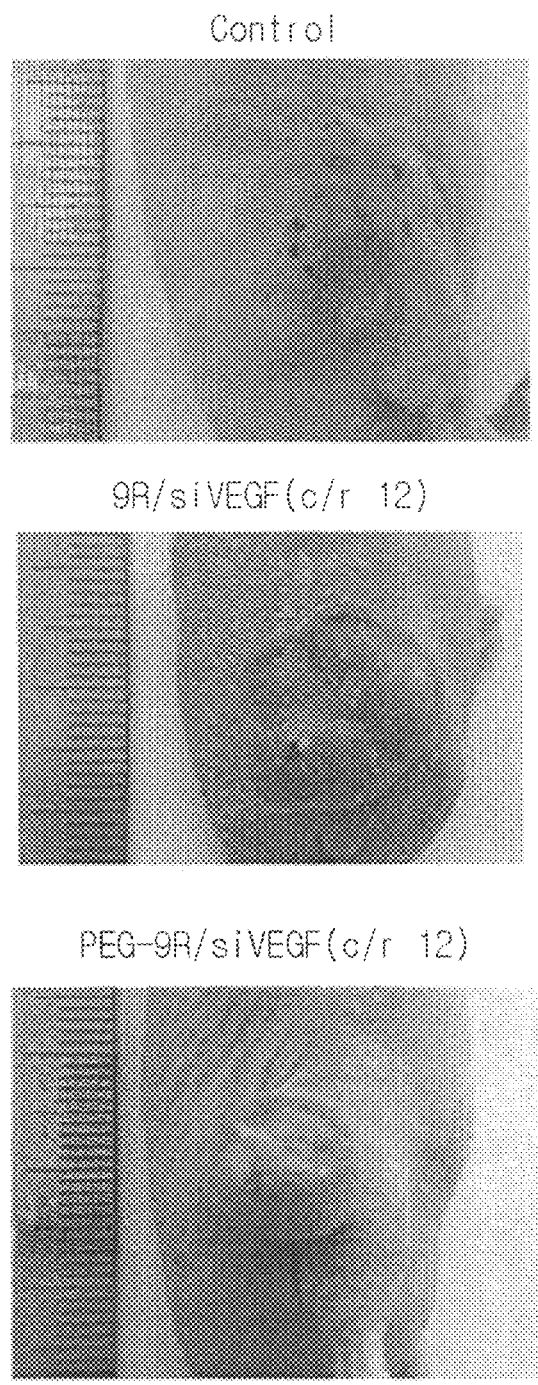
FIG. 10 shows images demonstrating the growth inhibition of cancer cells in cancer-transplanted nude mice 10 days after administration of siVEGF polyplexes.

The results are shown in FIGS. 9 and 10. A lower tumor growth rate was observed in the PEG-R9/siVEGF complex-administered group than in the other complex-administered groups, demonstrating superior anticancer effect of the PEG-R9/siVEGF complexes.

The invention claimed is:

1. A siRNA delivery system for systemic circulation consisting of polyethylene glycol (PEG) and a nona-arginine (R9) peptide, wherein the nona-arginine (R9) peptide has a Cys-(D-R9)-Cys or Gly-(D-R9)-Cys structure.

2. A complex for siRNA delivery for systemic circulation consisting of polyethylene glycol (PEG), a nona-arginine (R9) peptide, and siRNA, wherein the nona-arginine (R9) peptide has a Cys-(D-R9)-Cys or Gly-(D-R9)-Cys structure.

3. The complex according to claim 2, wherein the nona-arginine (R9) peptide has a Cys-(D-R9)-Cys structure.

4. The complex according to claim 2, wherein the polyethylene glycol (PEG) is PEG500 having a molecular weight of 500 daltons.

5. The complex according to claim 2, wherein the complex has a diameter of 200 nm or less.

6. The complex according to claim 2, wherein the complex has a charge ratio (+/−) of 6:1 to 15:1.

7. The complex according to claim 6, wherein the complex has a charge ratio (+/−) of 12:1.

8. A complex for the delivery of siRNA for anticancer use containing treating cancer, the complex consisting of polyethylene glycol (PEG), a nona-arginine (R9) peptide, and siVEGF, wherein the nona-arginine (R9) peptide has a Cys-(D-R9)-Cys structure.

9. A composition for the treatment of a VEGF-overexpressing cancer containing the complex according to claim 8 as an active ingredient.

10. The composition according to claim 9, wherein the VEGF-overexpressing cancer is selected from lung cancer, gynaecological malignancy, melanoma, breast cancer, pancreatic cancer, ovarian cancer, uterine cancer, colorectal cancer, prostate cancer, renal cancer, head cancer, pancreatic cancer, liver cancer or hapatocellular cancer, uterine cancer, neck cancer, renal cancer or renal cell carcinoma, sarcoma, myeloma, and lymphoma.

* * * * *